US009238617B2

(12) United States Patent
Verborgt et al.

(10) Patent No.: US 9,238,617 B2
(45) Date of Patent: *Jan. 19, 2016

(54) POLYUREAS MADE FROM AMINOCROTONATES

(71) Applicants: Jozef Verborgt, Dunedin, FL (US); Arthur A. Webb, Bethesda, MD (US)

(72) Inventors: Jozef Verborgt, Dunedin, FL (US); Arthur A. Webb, Bethesda, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,365

(22) Filed: Apr. 30, 2015

(65) Prior Publication Data

US 2015/0232416 A1  Aug. 20, 2015

Related U.S. Application Data

(60) Division of application No. 14/264,459, filed on Apr. 29, 2014, now Pat. No. 9,051,489, which is a continuation-in-part of application No. 12/465,068, filed on May 13, 2009, now Pat. No. 8,710,170.

(60) Provisional application No. 61/053,226, filed on May 15, 2008.

(51) Int. Cl.
| | |
|---|---|
| *C07C 221/00* | (2006.01) |
| *C07C 223/00* | (2006.01) |
| *C07C 225/00* | (2006.01) |
| *C07C 211/00* | (2006.01) |
| *C07C 229/30* | (2006.01) |

(52) U.S. Cl.
CPC ..................... *C07C 229/30* (2013.01)

(58) Field of Classification Search
CPC ......................................... C07C 225/14
USPC ............................. 528/68; 564/502
See application file for complete search history.

(56) References Cited

U.S. PATENT DOCUMENTS 4,284,752 A * 8/1981 Haug ............................. 528/68

* cited by examiner

*Primary Examiner* — David Karst
(74) *Attorney, Agent, or Firm* — US Naval Research Laboratory; Joseph T. Grunkemeyer

(57) ABSTRACT

A compound having the formula below, where R is —H or —CH$_2$—CH$_3$; n, x, y, and z are nonnegative integers; R$^2$ is an aliphatic group or oxyaliphatic group; and R$^3$ is an aliphatic group.

1 Claim, No Drawings

POLYUREAS MADE FROM AMINOCROTONATES

This application is a divisional application of allowed U.S. patent application Ser. No. 14/264,459, filed on Apr. 2, 2014, which is a continuation-in-part application of U.S. Pat. No. 8,710,170, filed on May 13, 2009 and issued on Apr. 29, 2014, which claims the benefit of U.S. Provisional Application No. 61/053,226, filed on May 15, 2008. The provisional application and all other publications and patent documents referred to throughout this nonprovisional application are incorporated herein by reference.

TECHNICAL FIELD

The present disclosure is generally related to polyureas.

DESCRIPTION OF RELATED ART

Polyurea coatings are based on the reaction of diamines and/or polyamines with isocyanate hardeners. They may be characterized by fast curing (e.g. seconds), a high elongation, a low tensile strength, and poor adhesion to blasted steel. Due to their composition and low glass transition temperature, they are also very permeable for water molecules. Polyureas with such properties may be unfit for marine use.

Poly-urea coatings are commonly used as truck bed liners, secondary containment coatings and by the military as blast mitigation coatings. Polyureas are also widely used in fast curing injection molding systems. The general structure of polyureas is shown below for a diamine having the formula $NH_2-R^1-NH_2$ and an isocyanate having the formula $OCN-X-NCO$.

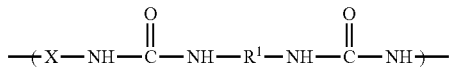

The polyamines used may in general be polyoxypropylene amines (Jeffamines), mixed with aromatic diamines. The isocyanate hardeners may be polymeric aromatic isocyanates with a very low vapor pressure. The very high reactivity of amines with isocyanates constitutes a limitation for this technology. For marine coatings applications, reducing this reactivity may be desirable.

Aspartics have been used as reagents for isocyanates (U.S. Pat. Nos. 5,126,170 and 5,236,741). Aspartic resins are the reaction products of aliphatic diamines with diethylmaleate via the Michael Addition Reaction. The idea behind the aspartics is to reduce the reactivity of the secondary NH by steric hindrance by the bulky aspartic moiety. The use of cycloaliphatic diamines with methyl groups in the alpha position results in further reduction of the NH reactivity. Aspartics contain the structure shown below.

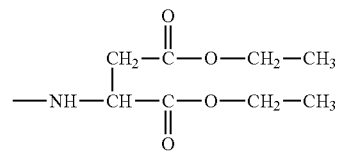

Existing commercially available aspartic resins do have interesting curing characteristics but they are too high in viscosity to allow for solvent free coatings in general. Aspartic resins may not be suitable for under water use in combination with cathodic protection systems.

Other well-known modifications of amines are ketimines and aldimines, which are the reaction products of primary amines with ketones or aldehydes. Their general structures are shown below.

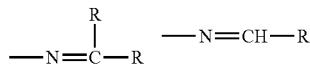

Ketimines and aldimines can react with isocyanates in several ways. Ketimines and aldimines may react with moisture from the atmosphere splitting off the ketone or aldehyde. The generated free amine will then react with the isocyanate group (US Patent Application Publication No. 2007/0060733). Although of interest this approach may not lead to solvent free coatings. Ketimines or aldimines may also be used as reactive diluents in polyurethanes, aspartics, and polyureas.

BRIEF SUMMARY

Disclosed herein is a compound having the formula below. R is $-H$ or $-CH_2-CH_3$. The values n, x, y, and z are nonnegative integers. $R^2$ is an aliphatic group or oxyaliphatic group and $R^3$ is an aliphatic group.

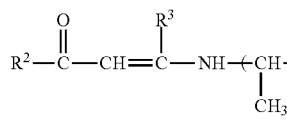

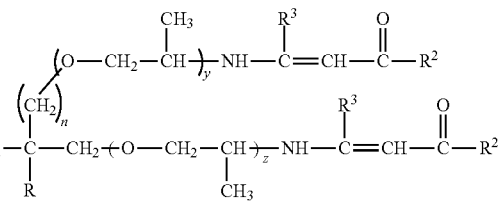

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is a modification of polyamines which may change the properties of the polyureas made therefrom.

Aliphatic polyamines such as Jeffamines are chemically modified into secondary amines with an improved gel time and different mechanical properties for the cured products. Without limiting the claims to any particular theory or reaction mechanism, it is believed that electron withdrawing groups may be used to reduce the basicity of the NH groups to achieve the same or similar NH reactivity as with aspartics without relying on steric hindrance. The reaction product of a enamine, enaminone, or crotonate with an isocyanate is an enurea.

Polyamines including aliphatic polyamines (which may include ether groups) can be reacted with one or more beta ketoesters like ethylacetoacetate or diketones like acetylacetone. These compounds may be made according to methods known in the art for making ketimines. Both ethylacetoacetate and acetylacetone are industrially available at low cost. They may react spontaneously with Jeffamines or other polyamines at ambient temperature. Water separates out and further drying can be done by either azeotropic distillation or the use of molecular sieves in the final formulation. The general reaction is shown below, followed by the products made from ethylacetoacetate and acetylacetone. Other suitable reactants include, but are not limited to, methylacetoacetate and t-butylacetoacetate.

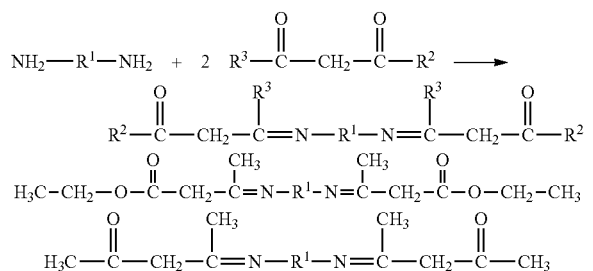

These compounds may be in equilibrium with the tautomer enamine β-aminocrotonate or β-aminoenone forms as shown below.

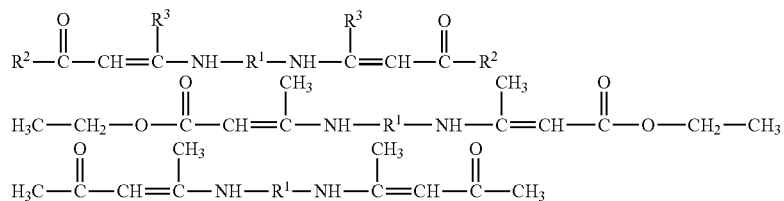

The $R^2$ and $R^3$ groups from at least one side of the $R^1$ may also be joined by a covalent bond to form a cyclic structure bonded to the amine. For example, the use of 1,3-cyclohexane-dione produces the aminoenone shown below.

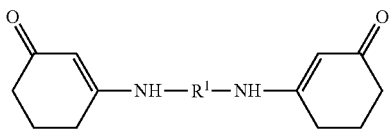

Any polyamine or multiple polyamines capable of forming ketimines may be used, including but not limited to, primary polyamines, m-xylylene diamine, diethylene triamine, (2-aminoethoxy)-2-aminoethane, 2-(2-aminoethoxy)ethanol, 1,5-diamino-2-methylpentane, N-methyl-1,3-aminopropane, $NH_2$—$(CH(CH_3))$—$CH_2$—$O)_x$—$CH_2$—$CH(CH_3)$—$NH_2$, $NH_2$—$(CH(CH_3))$—$CH_2$—$O)_x$—$(CH_2$—$CH_2$—$O)_y$—$(CH(CH_3))$—$CH_2$—$O)_z$—$CH_2$—$CH(CH_3)$—$NH_2$, $NH_2$—$(CH_2)_x$—$O$—$CH_2$—$CH_2$—$O$—$(CH_2)_x$—$NH_2$, or $NH_2$—$(CH(CH_3))$—$CH_2$—$O)_x$—$CH_2$—$CR[(CH_2)_n$—$(O$—$CH_2$—$CH(CH_3))_y$—$NH_2]$—$CH_2$—$(O$—$CH_2$—$CH(CH_3))_z$—$NH_2$.

In these formulas n, x, y, and z are nonnegative numbers, including but not limited to 0, 1, 2, 3, 4, 5, 6, 7, 8, 9, 10, and higher values, and may represent average values of a mixture of such compounds. The compounds containing ethoxy groups are commercially available as JEFFAMINES®, including the D series, ED series, EDR series, and T series. The polyamine need contain at least two reactive amines, though some amines may possibly remain unreacted in the polymer. If there are three or more amine groups, it is not necessary that all the amines be reactive to form ketimines, such as secondary or tertiary amines. If there are only two reactive amines in the compound (bi functional), than the polyisocyanate may have at least three isocyanate groups (at least trifunctional). If the amine has at least three reactive amines, than a diisocyanate may be used. It should be noted that both reactants may also be trifunctional or more.

The electron withdrawing effect across the double bond and subsequent reduction in NH reactivity may be more efficient than in the case of the aspartics. The general reaction with a polyisocyanate is shown below for the case of a diamine and a diisocyanate. The $R^1$ group may contain additional reactive amines, including —NH—$CR^3$=CH—CO—$R^2$, and/or the $R^4$ group may contain additional isocyanate group to form a crosslinked polymer. Since combinations of multiple reactants may be used, the R groups may be different in different repeat units of the polymer.

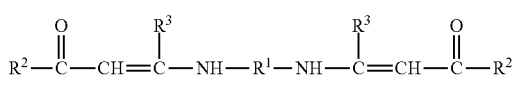

+

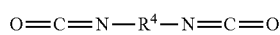

↓

-continued

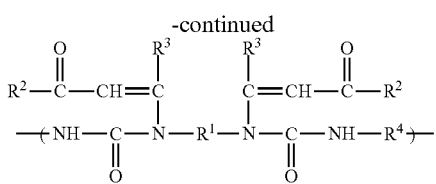

Any reactive isocyanate may be used optionally subject to the functionality requirement described above, including but not limited to, diphenylmethane-containing polyisocyanate, toluene diisocyanate, diphenyl methane diisocyanate, hexamethylene diisocyanate dimers and trimers, 4,4'-dicyclohexylmethane-diisocyanate, isophorone diisocyanate, tetramethylxylene diisocyanate, hexamethylene diisocyanate, cycloaliphatic polyisocyanates, aliphatic polyisocyanates, adduct of toluene diisocyanate and glycerin, biuret of toluene diisocyanate, and biuret of hexamethylene diisocyanate. More than one isocyanate may be used in a polymer. At least 50 mol % of the polyisocyanate molecules reacting with the polyamine are aromatic polyisocyanates having at least one aromatic group. The aromatic group may have double bonds conjugated with the isocyanate groups. Any purely aliphatic polyisocyanates would be less than 50, 20, 10, 5, or 1 mol % of the polyisocyanates, or aliphatic polyisocyanates may be completely absent.

Any method of combining the isocyanate with the above compounds may be used to form the polymer. One suitable method of combining is to apply to a surface an amine composition comprising the above compounds and an isocyanate composition comprising the polyisocyanate, such that a mixture of the amine composition and the isocyanate composition is formed during the application. For example, the application may be by spraying the compositions onto the surface and allowing the mixture to cure to a polyurea coating. Additional coating methods and formulation components are disclosed in US Patent Application Publication Nos. 2007/0060733 and 2007/0261602.

The reactants may have relatively low viscosities, and be liquid at room temperature. Thus the reaction may be performed in the substantial absence of solvent or in a lack of solvent. When no solvent is used, no volatile compounds are released during the reaction. There may be less than 5 or 1 wt % of any solvents or liquids other than the two reactants. The reaction may be performed at room temperature or at ambient temperature without external or active heating.

The reaction products of these crotonates and aminoenones may show improved mechanical properties, beyond what can be achieved with aspartics and/or polyureas. Some characteristic properties of the cured products may include:
VOC and HAPS: zero
Viscosity of base resin: 1,000 cps Brookfield
Equivalent NH weight: 240-300
Tensile strength: 7,000 -10,000 psi
Elongation at break for clear films: 10-20%
Glass transition: 90-125° C.
Tack free time at 20° C.: 10 minutes
Good mechanical properties: 12 h
Full cure: 3 to 5 days
Over coating interval: 3 to 5 days
Direct adhesion to blasted steel: excellent
Raw material cost for base resin: US$ 2/lbs
The resin system may be formulated into coatings with a 1 to 1 or 2 to 1 ratio. The coatings have zero VOC or HAPS and may be dry to touch in ten minutes. Good mechanical properties may be obtained overnight and full cure after 3 to 5 days. The fully cured material or coating may be free of any solvents or liquids. New upcoming International Maritime Organization (IMO) rules may result in a serious loss of productivity in the ship building industry. The new polyurea may offer increased productivity due to the curing rate and the possibility of single coat "multi pass" application, combined with a suitable over coating window.

As water scavengers, molecular sieves, p-toluene sulfonyl isocyanate, vinyl silanes or other silanes or any other way of drying the resins and pigments may be used as is normally done in the polyurethane industry.

The modified polyamines are also candidates for improved composite materials and injection molding materials. By varying the backbone of the diamines and polyamines it is possible to freeze in the curing reaction at ambient temperature in order to make prepregs. The prepregs can then be fully formed and heat cured at a later stage. Glass transition temperatures of up to 125° C. with a curing time of 10 minutes at 90° C. have been obtained.

The following examples are given to illustrate specific applications. These specific examples are not intended to limit the scope of the disclosure in this application. All reactions are carried out in a three necked flask, equipped with a mechanical stirrer or magnetic stirring bar.

EXAMPLE 1

Crotonate of MXDA—To the reactor were added 5 moles of m-xylylene diamine (680 grams) and 10 moles of ethyl acetoacetate. The reaction was slightly exothermic. The reactor was equipped with a distillation head and the mixture was slowly heated to remove the reaction water. The removal of the reaction water can be done either at ambient pressure or under reduced pressure or by means of an azeotropic distillation using hexane, cyclohexane, toluene, xylene, or other. At ambient pressure the reaction was virtually complete when all the reaction water is removed (180 grams) at about 145° C.

It is possible to make use of a combination of a reduced pressure, ambient pressure, and/or an azeotropic distillation process. Residual water content can be as low as 5 ppm. In order to push the reaction to completion it may be advantageous to use a slight excess of one of the ingredients, such as the ethyl acetoacetate. The reaction between the amine and ethyl acetoacetate is spontaneous and does not require the use of any catalyst. The obtained bifunctional amino crotonate can be cured advantageously with aromatic polyfunctional isocyanates.

EXAMPLE 2

Crotonate of Jeffamine D230—850 grams of Jeffamine D230 (7.39 molar equivalent weight) and 960 grams of ethyl acetoacetate were reacted as in Example 1. The resulting NH equivalent weight was 227.

EXAMPLE 3

Crotonate of Jeffamine T403—521 grams of Jeffamine T403 (3.21 molar equivalent weight) were reacted with 423 grams of ethyl acetoacetate as in Example 1. The resulting NH equivalent weight of the polymer was 274.

EXAMPLE 4

Enaminone of Jeffamine T403—1001 grams of Jeffamine T403 (6.18 molar equivalent weight) were reacted with 803 grams of ethyl acetyl acetone as in Example 1. A small excess of 20 grams of ethyl acetoacetate was added. The resulting NH equivalent weight was 244.

EXAMPLE 5

Crotonate of diethylene triamine—160 grams of diethylene triamine (DTA) (1.55 molar equivalent) was reacted with 403 grams of ethyl acetoacetate as in Example 1. The resulting product was rather dark in color but cured well with aromatic isocyanates. The resulting crotonate NH equivalent weight was 164. Note that the product still has the NH amine functionality in the middle.

EXAMPLE 6

Enaminone of glycol amine—420 grams of glycolamine (4 moles) were reacted with 4 moles of acetyl acetone as in Example 1. The reaction was exothermic and cooling was required. The resulting product had a NH equivalent weight of 187.

EXAMPLE 7

Crotonate of Dytek A (methyl diamino pentane)—2 moles of Dytek A were reacted with 4 moles of ethyl acetoacetate as in Example 1. The resulting product had an NH equivalent weight of 129.

EXAMPLE 8

Crotonate of N-methyl-1,3-propane diamine—2 moles of N-methyl-1,3-propane diamine were reacted with 2 moles of ethyl acetoacetate as in Example 1. The resulting crotonate NH functionality was 200. Note that the product still had the NH-CH3 functionality at the other end.

EXAMPLE 9

Crotonate of Jeffamine XTJ566—950 grams of XTJ566 (6.5 equivalent weight) were reacted with 851 grams of ethyl acetoacetate as in Example 1. A small excess of ethyl acetoacetate (50 grams) was added to facilitate the completion of the reaction. The resulting NH functionality of the resin obtained was 257.

EXAMPLE 10

Crotonate of Jeffamine EDR176—750 grams of EDR176 (8.5 equivalent weight) were reacted with 1108 grams of ethyl acetoacetate as in Example 1. The resulting product had an NH equivalent weight of 200.

EXAMPLE 11

Enaminone of Jeffamine T403—1100 grams of Jeffamine T403 (6.79 equivalent weight) were reacted with 680 grams of ethyl acetone as in Example 1. The reaction water was removed azeotropically with cyclohexane and followed with a vacuum distillation the resulting product was light in color and had an enaminone NH functionality of 244. The residual moisture content of the resin was lower than 10 ppm.

EXAMPLE 12

Enaminone of Jeffamine D230—1000 grams of Jeffamine D230 (8.69 equivalent weight) were reacted with 869 grams of acetyl acetone as in Example 1. The resulting product had an enaminone equivalent weight of 197.

EXAMPLE 13

Solvent free fast curing polycrotonate—2000 grams of T403 crotonate resin (equivalent weight of 274) were mixed in a cowless mixer with 1000 grams of $TiO_2$ pigment, 600 grams of Talcum filler, 35 grams of Byk 163 wetting agent, and 15 grams of coroc flow additive. As a water scavenger, 100 grams of molecular sieves were added.

The resulting paint can be cured with aromatic isocyanates like Mondur CD, MRS4, MRS light (all Bayer) and Rubinate M and or suprasec 9584 from Huntsman Chemicals. This example can be performed with any of the monomers and isocyanates disclosed herein. The amounts of the materials may be varied.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A compound having the formula:

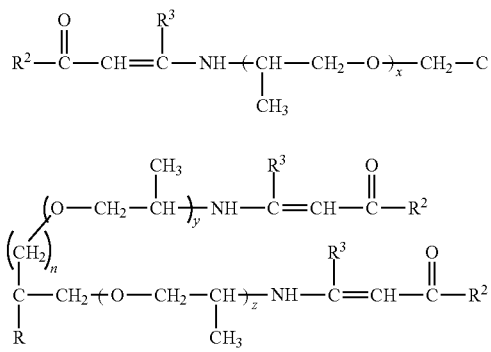

wherein R is —H or —$CH_2$—$CH_3$;
wherein n is a nonnegative integer;
wherein x, y, and z are positive integers;
wherein $R^2$ is an aliphatic group or oxyaliphatic group; and
wherein $R^3$ is an aliphatic group.

* * * * *